(12) United States Patent
Wang

(10) Patent No.: US 8,722,701 B2
(45) Date of Patent: May 13, 2014

(54) 1,2,3,4,5 6,7,8-OCTOHYDRO-9-PHENYLACETAMIDOACRIDINE, THE PREPARATION METHOD AND MEDICAL USE THEREOF

(75) Inventor: Tonghui Wang, Jilin (CN)

(73) Assignees: Changchun Huayang High Technology, Inc., Jilin (CN); Jiangsu Shen ER Yang High Technology Co., Ltd., Jiangsu (CN)

( * ) Notice: Subject to any disclaimer, the term of this patent is extended or adjusted under 35 U.S.C. 154(b) by 0 days.

(21) Appl. No.: 13/700,395

(22) PCT Filed: Sep. 2, 2011

(86) PCT No.: PCT/CN2011/079272
§ 371 (c)(1),
(2), (4) Date: Feb. 11, 2013

(87) PCT Pub. No.: WO2012/031534
PCT Pub. Date: Mar. 15, 2012

(65) Prior Publication Data
US 2013/0158065 A1    Jun. 20, 2013

(30) Foreign Application Priority Data
Sep. 10, 2010    (CN) .......................... 2010 1 0277579

(51) Int. Cl.
*A01N 43/42* (2006.01)
*A61K 31/44* (2006.01)
*C07D 219/10* (2006.01)

(52) U.S. Cl.
USPC ........................... 514/297; 546/105

(58) Field of Classification Search
CPC ............................ C07D 219/10; C07D 471/04
USPC ........................... 514/297; 546/105
See application file for complete search history.

(56) References Cited

U.S. PATENT DOCUMENTS 4,985,430 A * 1/1991 Morita et al. ............ 514/253.02
5,397,785 A 3/1995 Ninomiya et al.
5,767,126 A 6/1998 Marchbanks

FOREIGN PATENT DOCUMENTS

CN    1523016 A    8/2004
EP    0282959 A2    9/1988

OTHER PUBLICATIONS

International Search Report issued on Dec. 8, 2011 for International Application No. PCT/CN2011/079272.
"Inorganic Pharmaceutical Chemistry," Remington's Pharmaceutical Sciences, Mack Pub. Co., Easton, Pa., 1980, in 9 pages.

* cited by examiner

*Primary Examiner* — Kendra D Carter
(74) *Attorney, Agent, or Firm* — Knobbe, Martens, Olson & Bear, LLP

(57) ABSTRACT

Disclosed are 1,2,3,4,5,6,7,8-octohydro-9-phenylacetamidoacridine and the salt thereof, as well as the preparation method and medical use thereof. The compound can be useful for the preparation of medicaments for treating cardiovascular diseases, especially arrhythmia.

6 Claims, 4 Drawing Sheets

1,2,3,4,5 6,7,8-OCTOHYDRO-9-PHENYLACETAMIDOACRIDINE, THE PREPARATION METHOD AND MEDICAL USE THEREOF

RELATED APPLICATIONS

This application is a U.S. National Phase of International Application No. PCT/CN2011/079272, filed Sep. 2, 2011, designating the U.S., and published in Chinese as WO 2012/031534 on Mar. 15, 2012 which claims the benefit of Chinese Patent Application No. 201010277579.8 filed Sep. 10, 2010.

FIELD OF THE ART

The invention relates to a novel compound, i.e. 1,2,3,4,5,6,7,8-octohydro-9-phenylacetamidoacridine and the pharmaceutical acceptable salt thereof, as well as the methods for preparing the same. The application further provides the use of the compound for the preparation of medicaments for treating cardiovascular diseases, thus belonging to the field of medical pharmaceutical art.

BACKGROUND OF THE INVENTION

The inventive 1,2,3,4,5,6,7,8-octohydro-9-phenylacetamidoacridine and the hydrochloride thereof are novel compounds and are disclosed for the first time herein. Their structurally similar compound 9-amino-1,2,3,4,5,6,7,8-octohydroacridine has been proved to have an inhibition activity for cholinesterase and thus useful for the treatment of senile dementia (Chinese Patent No: ZL 03104541.3). In addition, U.S. Pat. No. 5,767,126 (Marchbanks and Roger) discloses the polyhydrogenated and dehydrogenated derivatives of 9-amino-1,2,3,4-tetrahydroacridine (Tacrine) which is used for treating senile dementia and has a hepatotoxicity. U.S. Pat. No. 4,942,237 discloses an acridine derivative called ISOXAZOLO (5,4,3-KL) ACRIDINE and its use for the treatment of pains and various memory dysfunctions.

DISCLOSURE OF THE INVENTION

The invention provides a novel compound, i.e. 1,2,3,4,5,6,7,8-octohydro-9-phenylacetamidoacridine and the pharmaceutical acceptable salt thereof, which are used for the treatment of cardiovascular diseases.

The invention also provides the methods for preparing the above compounds. Such methods are suitable for industrial production.

The invention also discloses the use of the above compounds for the preparation of medicaments for treating cardiovascular diseases.

The Inventive 1,2,3,4,5,6,7,8-Octohydro-9-Phenylacetamidoacridine has the Structural Formula Shown as Follow:

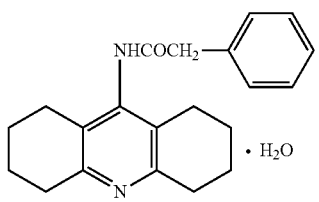

Molecular weight: 338.2; molecular formula: $C_{21}H_{24}N_2O \cdot H_2O$; melting point (° C.): 234-236.

The Method for Preparing the Inventive 1,2,3,4,5,6,7,8-Octohydro-9-Phenylacetamidoacridine Comprises the Steps Shown as Follows:

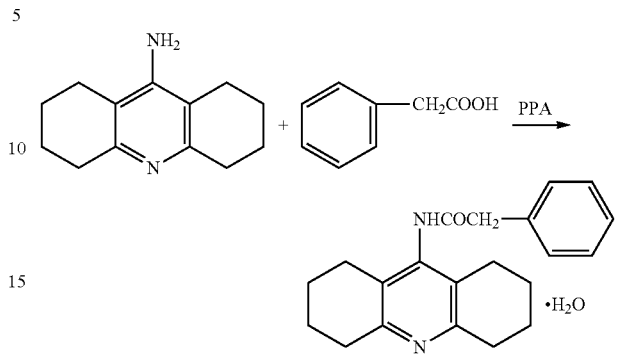

First, 5.0 g of 9-amino 1,2,3,4,5,6,7,8-octohydroacridine and 3.36 g of phenylacetic acid are weighted and added to a reaction bottle, to which 25 ml polyphosphoric acid is then added. The mixture is then heated to a temperature of 110-130° C. and allowed to react for 5 hours. After the reaction, about 1000 ml water is added for dissolution. A white precipitate is produced when the pH is adjusted to pH 5~6 with a KOH solution. After filtering off and drying, the white precipitate is recrystallized with methanol and acetone, and then filtered off to get said compound.

Upon detection, it is found that the compound prepared in the invention has a melting point of 234-236° C. Elemental analysis theoretical values, C: 74.57%, H: 7.68%, N: 8.28%; and measured values, C: 74.28%, H: 7.57%, N: 7.98%.

1,2,3,4,5,6,7,8-octohydro-9-phenylacetamidoacridine and the pharmaceutical acceptable salts thereof may also be prepared with inorganic or organic acids by similar methods. For example, its hydrochloride has a structural formula shown as follow:

Molecular weight: 356.90; molecular formula: $C_{21}H_{24}N_2O \cdot HCL \cdot H_2O$; melting point (° C.): 231-234° C.

Upon detection, it is also found that the hydrochloride has a melting point of 231-234° C. Elemental analysis theoretical values, C: 68.97%, H: 7.10%, N: 7.66%; and measured values, C: 68.95%, H: 6.95%, N: 7.36%.

The Following Experiments Demonstrate the Medical Use of the Inventive 1,2,3,4,5,6,7,8-Octohydro-9-Phenylacetamidoacridine and the Hydrochloride Thereof for the Preparation of Medicaments for Treating Arrhythmia Diseases.

Objective:

To observe the effect of the invention compound and the hydrochloride thereof on medicament-induced experimental arrhythmia.

Method:

Models of experimental arrhythmia induced by aconitine and ouabain in rats and guinea pigs were constructed. The inventive compound and the hydrochloride thereof were administrated with dosages of 100 and 200 mg/kg, respectively. The positive medicament group was administrated with 10 mg/kg of Propranolol, and the control group was administrated with 0.5% carboxymethylcellulose sodium. Each group was administrated by gastric perfusion once. The occurrence times of ventricular premature contraction (VP), ventricular tachycardia (VT), ventricular fibrillation (VF) and cardiac arrest (CA) after administration of aconitine in rats were recorded; and the dosages of ouabain were also observed when VP, VT, VF and CA appeared.

Result:

The low and high dosage groups of the inventive compound and the hydrochloride thereof both had a significant antagonistic action on aconitine-induced arrhythmia in rats, and also markedly increased the dosages of ouabain when VP, VT, VF and CA occurred after administration of ouabain in guinea pigs. The actions of the inventive compound and the hydrochloride thereof were comparable to that of the positive medicament, i.e. Propranolol. In addition, the hydrochloride had an action slightly higher than its base (the inventive compound).

Conclusion:

The inventive compound and the hydrochloride thereof have an anti-arrhythmia property.

1. Materials and Methods 1.1 Animals

Wistar rats, 1:1 of females to males, weighted 205~250 g, provided by the Experimental Animal Center of Bethune Medical School of Jilin University, with the Animal Certificate No. SCXK (Ji) 2007-0003; and EWG/B guinea pigs, 1:1 of females to males, weighted 300~350 g, provided by the Experimental Animal Center of Bethune Medical School of Jilin University, with the Animal Certificate No. SCXK (Ji) 2007-0004.

1.2 Reagents

The inventive compound and the hydrochloride thereof were provided by Huayang High Tech Ltd. of Changchun. The Batch Nos. 20091105 (the inventive compound) and 20091105-1 (the hydrochloride of the inventive compound) were prepared into the desired concentration with 0.5% carboxymethylcellulose sodium during the experiments. Propranolol tables (10 mg/table) were purchased from Lisheng Pharmaceutics Ltd. of Tianjin, with the Batch No. 20080511.

1.3 Aconitine-Induced Arrhythmia in Rats

Sixty Wistar rats were divided into 6 groups randomly: a control group, a positive medicament (Propranolol) group, high- and low-dosage groups (200 and 100 mg/kg) of the inventive compound and the hydrochloride thereof, respectively, 10 animals per group. Fifty minutes after intragastric administration, the animals of each groups were anaesthetized by injecting 10% chloral hydrate intraperitoneally and fixed in a supine position. A type II lead normal electrocardiogram was then recorded. After that, 20 µg/kg of aconitine was injected via sublingual vein, and the change of the electrocardiogram was observed. The occurrence times of ventricular premature contraction (VP), ventricular tachycardia (VT), ventricular fibrillation (VF) and cardiac arrest (CA) after administration of aconitine in the rats were recorded.

1.4 Uabaina-Induced Arrhythmia in Guinea Pigs

Thirty-six guinea pigs were divided into 6 groups randomly: a control group, a positive medicament (Propranolol) group, high- and low-dosage groups (200 and 100 mg/kg) of the inventive compound and the hydrochloride thereof, respectively, 6 animals per group. Fifty minutes after intragastric administration, the animals of each groups were anaesthetized by injecting 10% chloral hydrate intraperitoneally and fixed in a supine position. After the external jugular vein was separated, intubation was performed and a constant-speed micro-infusion apparatus was installed. Then a type II lead normal electrocardiogram was recorded. After that, ouabain was infused via the external jugular vein at a constant rate of 5 µg/min, and the change of the electrocardiogram was observed. The dosages of ouabain when VP, VT, VF and CA occurred after administration of ouabain in the guinea pigs were recorded.

1.5 Statistic Analysis

The experimental data were analyzed with the statistic software SPSS 10.0, and represented as $x \pm s$. The comparison among groups was analyzed by the intergroup comparison difference t test.

2. Results 2.1 The Effect of the Inventive Compound and the Hydrochloride Thereof on Aconitine-Type Arrhythmia in Rats Compared with the control group, 10 mg/kg of the positive medicament, i.e. Propranolol, could markedly delay the occurrence times of ventricular premature contraction (VP), ventricular tachycardia (VT), ventricular fibrillation (VF) and cardiac arrest (CA) after administration of aconitine in the rats ($p<0.01$). Bothe the high- and low-dosage groups of the inventive compound and the hydrochloride thereof significantly delayed the occurrence times of VP, VT, VF and CA after administration of aconitine in the rats ($p<0.01$~$p<0.001$). The function of the inventive compound and the hydrochloride thereof was comparable to that of the positive medicament, i.e. Propranolol (see Table 1).

TABLE 1

The effect of the inventive compound and the hydrochloride thereof on aconitine-type arrhythmia in rats (n = 10, $x \pm s$)

| Groups | Dose (mg/kg) | Occurrence time (sec) | | | |
|---|---|---|---|---|---|
| | | VP | VT | VF | CA |
| Control group | 0 | 8.3 ± 3.1 | 51.9 ± 14.9 | 287.0 ± 53.2 | 562.0 ± 150.8 |
| Propranolol | 10 | 23.6 ± 6.9*** | 101.6 ± 32.5*** | 705.6 ± 233.2*** | 913.7 ± 208.6*** |
| Inventive compound | 100 | 16.9 ± 8.3** | 82.7 ± 21.0** | 621.6 ± 203.7*** | 910.1 ± 276.5** |
| | 200 | 20.7 ± 6.9*** | 95.6 ± 20.6*** | 650.4 ± 193.3*** | 905.7 ± 170.3** |
| Hydrochloride of the inventive compound | 100 | 17.3 ± 7.8** | 84.4 ± 19.0** | 640.4 ± 217.3*** | 907.2 ± 250.6** |
| | 200 | 22.6 ± 6.1*** | 98.6 ± 21.3*** | 660.2 ± 204.7*** | 911.2 ± 186.4** |

Compared with the control group,
*$p < 0.05$,
**$p < 0.01$,
***$p < 0.001$ 2.2 Change of the Electrocardiogram of Ouabain-Type Arrhythmia in Guinea Pigs Compared with the control group, 10 mg/kg of the positive medicament i.e. Propranolol could markedly increase the dosages of ouabain at the time VP, VT, VF and CA occurred after administration of ouabain in the guinea pigs ($p<0.05$~$p<0.001$). The high- and low-dosage groups of the inventive compound and the hydrochloride thereof significantly increased the dosages of ouabain at the time VP, VT, VF and CA occurred after administration of ouabain in the guinea pigs ($p<0.05$~$p<0.001$). The function of the inventive compound and the hydrochloride thereof was comparable to that of the positive medicament, i.e. Propranolol (see Table 2).

TABLE 2

The effect of the inventive compound on ouabain-type arrhythmia in guinea pigs (n = 6, x ± s)

| Groups | Dose (mg/kg) | Dosages of ouabain (μg/kg) | | | |
|---|---|---|---|---|---|
| | | VP | VT | VF | CA |
| Control group | 0 | 115.6 ± 28.6 | 135.8 ± 19.2 | 153.9 ± 18.8 | 219.2 ± 37.8 |
| Propranolol | 10 | 201.3 ± 55.6** | 240.7 ± 48.78*** | 323.2 ± 71.4*** | 390.6 ± 64.4*** |
| Inventive compound | 100 | 174.9 ± 41.7* | 184.1 ± 28.8* | 230.5 ± 46.4** | 283.0 ± 46.5* |
| | 200 | 185.5 ± 24.8** | 228.3 ± 36.6*** | 294.5 ± 51.9*** | 371.3 ± 69.6** |
| Hydrochloride of the inventive compound | 100 | 171.8 ± 38.4* | 189.7 ± 30.3* | 235.3 ± 36.3** | 280.3 ± 41.5* |
| | 200 | 189.5 ± 25.4** | 230.4 ± 35.3*** | 298.7 ± 49.1*** | 370.4 ± 66.7** |

Compared with the control group,
*p < 0.05,
**p < 0.01,
***p < 0.001

3. Discussion

Different types of arrhythmia can be induced by medicaments. Aconitine can activate the sodium pathway of myocardial cells, accelerate $Na^+$ influx into myocardial cells, cause depolarization of cell membrane, and result in multifocal ventricular arrhythmia by inducing ectopic rhythm point. Ouabain can inhibit $Na^+$- and $K^+$-ATPases directly, result in a loss of Potassium in myocardial cells, cause reduction of electrostatic potential and maximum diastolic potential in myocardial tissue, induce higher myocardial automaticity, and result in unidirectional block in Purkinje fiber and ventricular muscle joint part so as to cause reentry. A toxic dose of ouabain can result in temporary depolarization, and cause oscillatory after-potential and further ectopic rhythm. Its symptoms include ventricular premature contraction, ventricular tachycardia, ventricular fibrillation and cardiac arrest.

It was demonstrated by the result of this experiment that the inventive compound and the hydrochloride thereof had significant antagonistic actions against the arrhythmia induced by aconitine in rats and the arrhythmia induced by ouabain in guinea pigs. Such antagonistic actions were comparable to that of the positive medicament, i.e. Propranolol. Additionally, the hydrochloride had a slightly stronger antagonistic action than that of the inventive compound itself.

Objective 2:

To observe the effect of the inventive compound on the experimental arrhythmia induced by coronary artery ligation in rats.

Method:

Models of experimental arrhythmia induced by coronary artery ligation in rats were constructed. The inventive compound was administrated in a dose of 50, 100, 200 mg/kg, respectively. The positive medication group was administrated with 50 mg/kg of Verapamil, and the control group was administrated with 0.5% carboxymethylcellulose sodium. Each group wa administrated by gastric perfusion once. The occurrence times and the incidence rates of ventricular premature contraction (VP), ventricular tachycardia (VT), ventricular fibrillation (VE) and cardiac arrest (CA) after coronary artery ligation in rats were recorded.

Result:

Compared with the sham operation group, the occurrence times of VP, VT, VF and CA were shortened remarkably in the rat model groups. Compared with the model groups, the occurrence times of VP, VT, VF and CA were markedly delayed in the high-dose group of the inventive compound, and the occurrence times of VP and CA were markedly delayed in the low-dose group of the inventive compound. The effect of the high-dose group was comparable to that of the positive medicament, i.e. Verapamil. In addition, compared with the sham operation group, the incidence rates of VT, VF and CA were increased remarkably in the rat model groups. Compared with the model groups, the incidence rates of VT, VF and CA were decreased markedly in the high-dose group and the incidence rates of VT, VF and CA were not remarkably influenced in the low-dose group. The effect of the high-dose group of the inventive compound was comparable to that of the positive medicament, i.e. Verapamil.

Conclusion:

The inventive compound had a significant antagonistic action against the experimental arrhythmia induced by coronary artery ligation in rats. Such an antagonistic action was comparable to that of the positive medicament, i.e. Verapamil.

1. Materials and Methods 1.1 Animals

Wistar rats, 1:1 of females to males, weighted 215~250 g, provided by the Experimental Animal Center of Bethune Medical School of Jilin University, with the Animal Certificate No: SCXK (Ji) 2007-0003.

1.2 Reagents

The inventive compound was provided by Huayang High Tech Ltd. of Changchun, with the Batch No. 20091105. In the experiment, the inventive compound was prepared into the desired concentration with 0.5% carboxymethylcellulose sodium. Verapamil hydrochloride tables (40 mg/table) were purchased from CENTRALPHARM Inc. of Tianjin, with the Batch No. 030301.

1.3 Statistic Analysis

The experimental data were analyzed with the statistic software SPSS 10.0, and represented as x±s. The intergroup comparison was analyzed by the intergroup difference comparison t test. The incidence rates were compared by $\chi^2$ test.

2. Results 2.1 The Effect on the Occurrence Time of Arrhythmia Induced by Coronary Artery Ligation in Rats Compared with the sham operation group, the occurrence times of VP, VT, VF and CA were shortened remarkably in the rat model groups ($p<0.01$ or $p<0.001$). Compared with the model groups, the occurrence times of VP, VT, VF and CA were markedly delayed in the medium-dose and high-dose groups of the inventive compound ($p<0.05$~$p<0.001$) and the occurrence times of VP and CA were markedly delayed in the low-dose group of the inventive compound ($p<0.05$). The effect of the high-dose group was comparable to that of the positive medicament, i.e. Verapamil, see Table 3.

TABLE 3

The effect of the inventive compound on the occurrence time of
arrhythmia induced by coronary artery ligation in rats (x ± s)

| Groups | Dose (mg/kg) | n | Occurrence times (Sec) | | | |
|---|---|---|---|---|---|---|
| | | | VP | VT | VF | CA |
| Sham operation group | 0 | 15 | 1059.1 ± 371.8 | 1200.0 ± 0.0 | 1200.0 ± 0.0 | 1200.0 ± 0.0 |
| Model group | 0 | 18 | 32.1 ± 13.5[###] | 621.3 ± 450.8[###] | 770.1 ± 417.1[###] | 948.0 ± 282.7[###] |
| Inventive compound | 50 | 14 | 82.3 ± 79.0* | 773.8 ± 344.3 | 930.5 ± 379.4 | 1141.8 ± 161.9* |
| | 100 | 14 | 90.1 ± 39.7*** | 920.5 ± 270.6* | 1148.3 ± 193.6** | 1163.4 ± 124.6* |
| | 200 | 16 | 107.3 ± 67.9*** | 1043.2 ± 247.1** | 1115.0 ± 138.8** | 1176.4 ± 729.2** |
| Verapamil | 50 | 17 | 868.0 ± 530.4*** | 1166.4 ± 138.2*** | 1176.0 ± 98.9*** | 1157.9 ± 250.5* |

Compared with the sham operation group,
[##]$p < 0.01$,
[###]$p < 0.001$; and compared with the model group,
*$p < 0.05$,
**$p < 0.01$,
***$p < 0.001$.

2.2 The Effect on the Incidence Rate of Arrhythmia Induced by Coronary Artery Ligation in Rats Compared with the sham operation group, the incidence rates of VT, VF and CA were increased remarkably in the rat model groups ($p<0.01$). Compared with the model groups, the incidence rates of VT, VF and CA were decreased markedly in the medium-dose and high-dose groups of the inventive compound ($p<0.05$ or $p<0.01$) but the incidence rates of VT, VF and CA were not remarkably affected in the low-dose group ($p>0.05$). The effect of the high-dose group was comparable to that of the positive medicament, i.e. Verapamil, see Table 4.

TABLE 4

The effect of the inventive compound on the incidence rate of
arrhythmia induced by coronary artery ligation in rats (x ± s )

| Groups | Dose (mg/kg) | n | Incidence rate of arrhythmia (%) | | |
|---|---|---|---|---|---|
| | | | VT | VF | CA |
| Sham operation group | 0 | 15 | 0 | 0 | 0 |
| Model group | 0 | 18 | 83.3[##] | 61.1[##] | 50.0[##] |
| Inventive compound | 50 | 14 | 42.8 | 35.7 | 21.4 |
| | 100 | 14 | 28.6* | 14.3* | 14.3* |
| | 200 | 16 | 12.5** | 12.5* | 12.5* |
| Verapamil | 50 | 17 | 5.9** | 5.9** | 23.5 |

Compared with the sham operation group,
[#]$p < 0.05$,
[##]$p < 0.01$; and compared with the model group,
*$p < 0.05$,
**$p < 0.01$.

3. Discussion

In this study, based on the observation of the antagonistic actions of the inventive compound against the Na$^+$ type arrhythmia in rats and the K$^+$ type arrhythmia in guinea pigs induced by medicaments (aconitine and ouabain), a model of experimental arrhythmia induced by coronary artery ligation in rats was further constructed, and an antagonistic action of the inventive compound against the Ca$^{2+}$ type arrhythmia was observed.

It was demonstrated by the result of this experiment that the inventive compound had a significant antagonistic action against the experimental arrhythmia induced by coronary artery ligation in rats and such an antagonistic action was comparable to that of the positive medicament, i.e. Verapamil.

Presently, it is commonly agreed by pharmacologists and clinic cardiologists that an ideal anti-arrhythmia medicament should act on the optimal targets, and affect at least 2 or more ion channels[1,2]. It is revealed in the study that both the inventive compound and the hydrochloride thereof have significant antagonistic actions against the experimental arrhythmia induced by two medicaments and the arrhythmia induced by coronary artery ligation. The intensities of these actions are comparable to those of the positive medicaments Propranolol and Verapamil respectively. Therefore, both the inventive compound and the hydrochloride thereof are worthy to be developed and utilized extensively, and the mechanisms of their anti-arrhythmia actions are desired to be explored.

The above experimental results also show that the inventive 1,2,3,4,5,6,7,8-octohydro-9-phenylacetamidoacridine and the salts thereof have an anti-arrhythmia activity and the like, thus they can be developed into clinic therapeutic medicaments having the above functional activities.

The inventive pharmaceutical composition comprises a therapeutically effective amount of 1,2,3,4,5,6,7,8-octohydro-9-phenylacetamidoacridine and the salts thereof with the above structural formula as the active component and one or more pharmaceutical acceptable carriers and/or excipients.

According to a preferred embodiment of the invention, besides the basic active components, said pharmaceutical composition further comprises one or more additional natural, chemically synthesized or recombinantly produced compounds with the similar or synergistic activities. Said additional components with the similar or synergistic activities include, but are not limited to the component with a dilatation activity for peripheral vessels, especially cerebral vessels, or other active pharmaceutical components with an anti-arrhythmias activity, etc.

Another object of the invention is to provide pharmaceutical compositions used for the treatment of the various diseases mentioned above. Said pharmaceutical compositions comprise a therapeutically effective amount of 1,2,3,4,5,6,7,8-octohydro-9-phenylacetamidoacridine and the salts thereof with the above structural formula as the active component and one or more pharmaceutical acceptable carriers and/or excipients.

Any methods known in the field of pharmaceutical industry (e.g. see Remington's Pharmaceutical Sciences, Mack Pub. Co., Easton, Pa., 1980) can be used for the manufacture of the inventive pharmaceutical composition in a unit dosage form suitable for oral or non-oral administration. A preparation suitable for parenteral administration may comprises conventional excipients such as sterile water or saline, polyethylene glycol, oil and hydrogenated naphthaline, etc. Particularly, biocompatible and biodegradable lactide polymer, lactide/glycolide co-polymer, polyoxyethylene/polyoxypropylene co-polymer can be used as excipients, so as to control the release of the active components. Other releasing systems that can be used for the inventive pharmaceutical composition include ethylene-vinyl acetate co-polymer particles, an osmotic pump, an implantable infusion system or liposome, and so on. A preparation suitable for inhalation administration may comprise excipients such as lactic acid, deoxycholic acid, and the like. Among other parenterally administrated preparations, one administrated rectally may comprise salicylic acid, and one administrated buccally may comprise glycocholate, for example.

More specifically, a tablet preparation can be manufactured through conventional methods by using an excipient such as lactose, glucose, sucrose, mannitol and methylcellulose, etc.; a disintegrating agent such as starch, sodium alginate, calcium carboxymethylcellulose and crystalline cellulose, etc.; a lubricant such as magnesium stearate and talc, etc.; a binder such as gelatin, polyvinyl alcohol, polyvinylpyrrolidone, methylcellulose and hydroxypropyl cellulose, etc.; a surfactant such as sucrose fatty acid ester and sorbitan fatty acid ester, etc.; and adjuvant constituents such as colorant, sweetener, flavor and dispersing agent, etc.

A granule preparation can be made through conventional methods by using an excipient such as lactose and mannitol, etc.; a disintegrating agent such as starch; and a binder such as gelatin. Alternatively, a powder can be made through conventional methods by using an excipient such as lactose and sucrose, etc. and capsules can be made through conventional methods by using gelatin, water, sucrose, acacia gum, sorbitol, glycerol, crystalline cellulose, magnesium stearate and talc, etc.

An injectable preparation can be manufactured through conventional methods by using a solvent such as water, physiological saline, vegetable oil (such as olive oil and peanut oil), ethyl oleate and propylene glycol, etc.; a solubilizer such as sodium benzoate, sodium salicylate and urethane, etc.; an isotonizing agent such as sodium chloride and glucose, etc.; an antibiotic such as penicillin, streptomycin and other antifungal agents, etc.; a preservative such as phenol, cresol, p-hydroxybenzoate, chlorobutanol, domiphen bromide and sorbic acid, etc.; an antioxidant such as ascorbic acid and sodium pyropyhosphate, etc. Under any circumstances, said injectable preparation should be sterile and flowable, and suitable for injection administration via an injector. In addition, said preparation should be stable and can tolerate the contamination caused by microbes such as bacteria and fungi under the conditions of production, transportation and storage.

In order to formulate a preparation suitable for topical administration, for example, an effective amount of 1,2,3,4,5,6,7,8-octohydro-9-phenylacetamidoacridine and the pharmaceutical acceptable salts thereof can be dissolved in water or other appropriate carriers or media, and mixed with a proper skin permeable agent such as dimethyl sulfoxide or laurocapram, so as to prepare into a spray or an aerosol. Moreover, by using an excipient such as glycerol, magnesium stearate, polyethylene glycol, polyacrylamide, cholesterol, lecithin, methylcellulose or carboxymethylcellulose, talc powder, lactose, glucosan and starch, etc., the inventive pharmaceutical composition can be prepared into an emulsion, cream, ointment, gel or suppository (such as a vaginal suppository or rectal suppository) suitable for topical administration or for transdermal or transmucosal administration.

Furthermore, the inventive pharmaceutical composition can also be prepared into a microcapsule formulation or liposome-encapsulating formulation by using known methods and adjuvant constituents in the field of pharmaceutical industry.

The inventive pharmaceutical composition comprises, in addition to 1,2,3,4,5,6,7,8-octohydro-9-phenylacetamidoacridine and the pharmaceutical acceptable salts thereof as the basic active component, one or more synthesized, natural or recombinantly produced additional active components compatible with the invention. For instance, these active components include, but are not limited to the components that also have an inhibition activity for acetylcholine esterase, improve the activity of cholinergic transmission in the central nervous system, the activity for stimulating muscarinic receptor and the dilation activity for cerebral vessels; the component with a dilatation activity for peripheral vessels, especially cerebral vessels; or other active pharmaceutical components with an anti-arrhythmias activity or an anti-depression activity, etc.

In general, the inventive pharmaceutical composition has an oral dosage of 0.1-100 mg/kg/day, preferably 1-80 mg/kg/day, and most preferably 5-50 mg/kg/day; an intraperitoneal or intramuscular injection dosage of 0.05-100 mg/kg/day, preferably 0.1-80 m/kg/day, and most preferably 0.5-50 mg/kg/day; and an intravenous injection dosage of 0.01-100 mg/kg/day, preferably 0.05-80 mg/kg/day, and most preferably 0.1-50 mg/kg/day. Apparently, it can be understood by those skilled in the art that for the sake of effective treatment of patients, the precise dosages should be determined by a clinic physician on an individual basis, depending on many factors such as the nature and severity of the condition or pathological state to be treated; age, weight and general health condition of the patient; dosage form of the medicaments used; sensitivity and tolerance of the patient to the employed medicaments; and the administration route to be taken, and so on.

The positive effect of the invention is that 1,2,3,4,5,6,7,8-octohydro-9-phenylacetamidoacridine and the salts thereof, as a novel compound, can be used in the preparation of medicaments for treating cardiovascular diseases, which further enhances and improves the biological activity of the medicaments, reduces the toxicity of the medicaments, and facilitates the absorption and release of the medicaments in vivo.

EMBODIMENTS FOR CARRYING OUT THE INVENTION

The following Examples are intended to illustrate, but not limit the invention. It should be understood by those skilled in the art that any parallel modifications and alterations made to the invention are within the scope defined by the claims attached herein, without deviation from the spirit and principle of the invention.

Example 1

Synthesis of the compound 1,2,3,4,5,6,7,8-octohydro9-phenylacetamidoacridine

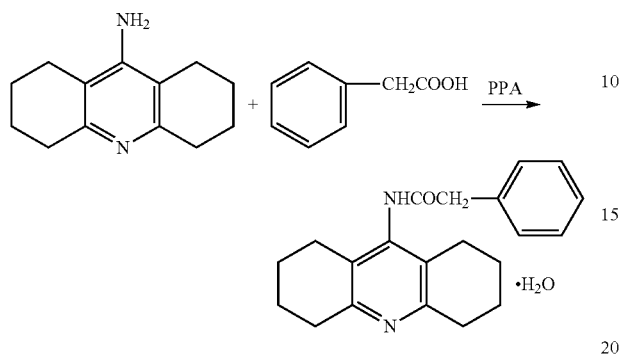

First, 5.0 g of 9-amino-1,2,3,4,5,6,7,8-octohydroacridine and 3.36 g of phenylacetic acid were weighted and added to a reaction bottle, to which 25 ml polyphosphoric acid was then added. The mixture was then heated to a temperature of 110-130° C. and allowed to react for 5 hours. After the reaction, about 1000 ml water was added for dissolution. A white precipitate was produced after the pH was adjusted to pH 5-6 with a KOH solution. After filtering off and drying, the white precipitate was recrystallized with methanol and acetone, and then filtered off to generate the subject compound.

Figure 1:
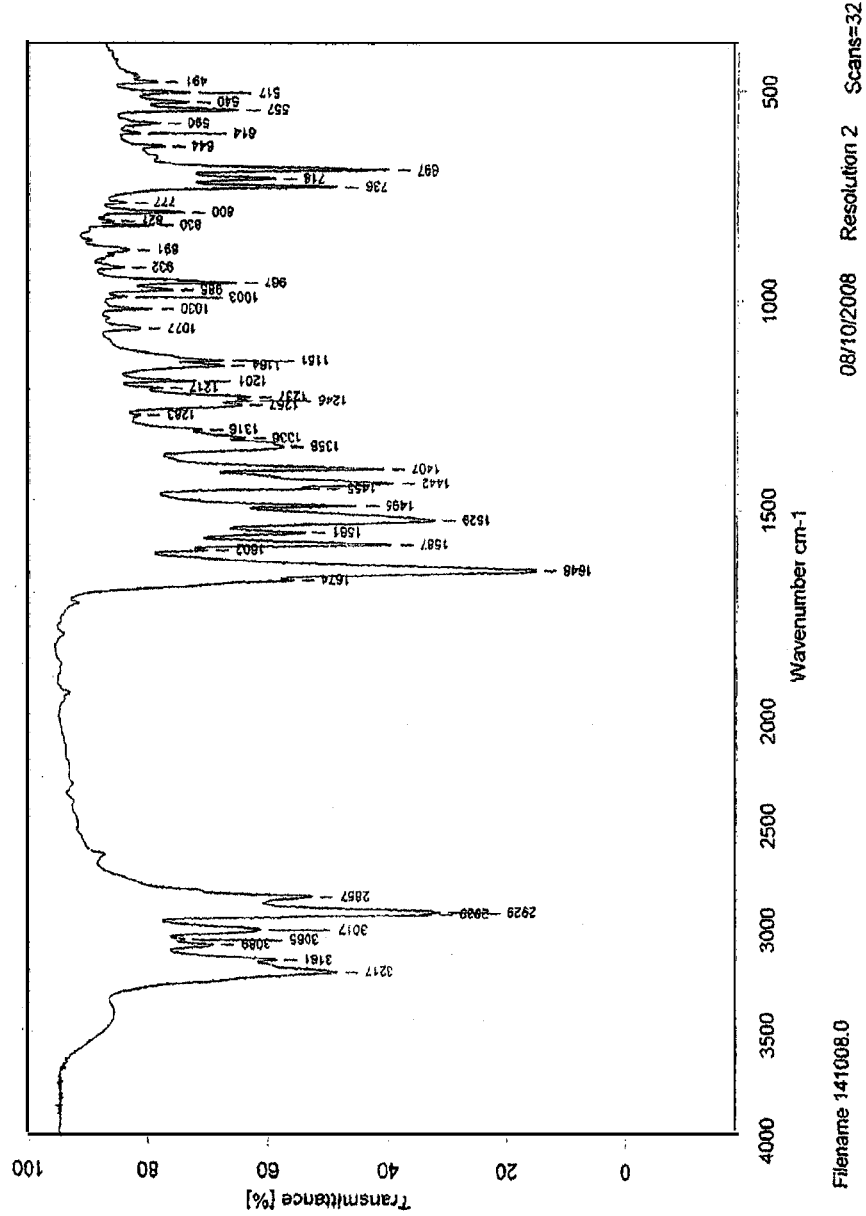
FIG. 1 is the $^1$H-NMR spectrum of 1,2,3,4,5,6,7,8-octohydro-9-phenylacetamidoacridine.
Figure 2:
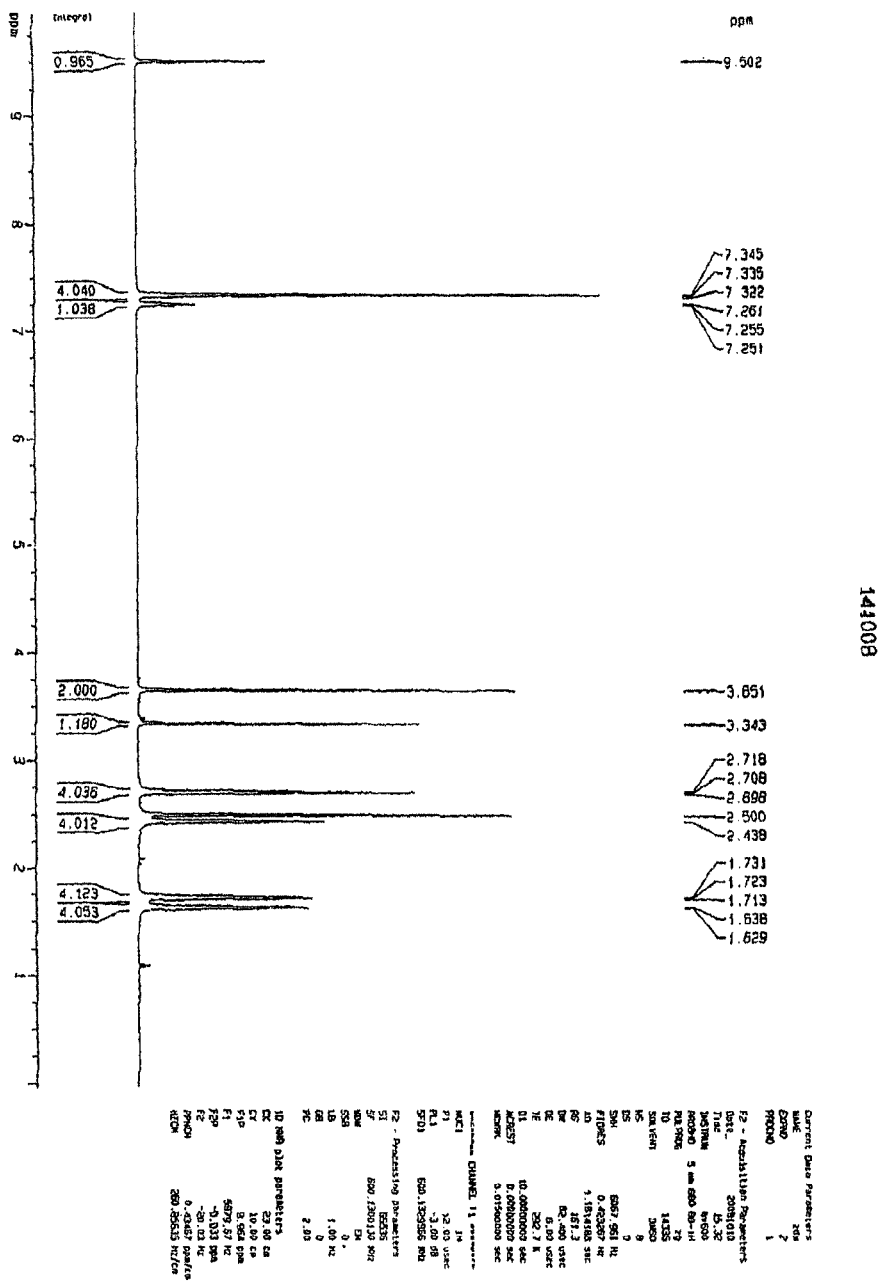
FIG. 2 is the infrared spectrum of 1,2,3,4,5,6,7,8-octohydro-9-phenylacetamidoacridine.

Molecular formula: $C_{21}H_{24}N_2O.H_2O$; molecular weight: 338.2; melting point (° C.): 234-236. The $^1$H-NMR spectrum and infrared spectrum of the compound were shown in FIGS. 1 and 2, respectively. The data in the 1H-NMR spectrum included: 9.50 (1H), 7.25-7.35 (5H), 3.65 (2H), 2.70 (4H), 2.50 (4H), 1.72 (4H), 1.63 (4H); and the data in the infrared spectrum included: 3217c., 3161, 3089, 3065, 3017, 1648c., 1587, 1561, 1529c., 1495, 1442, 1356, 736, 697.

Example 2

Synthesis of the Compound—The Hydrochloride of 1,2,3,4,5,6,7,8-octohydro9-phenylacetamidoacridine

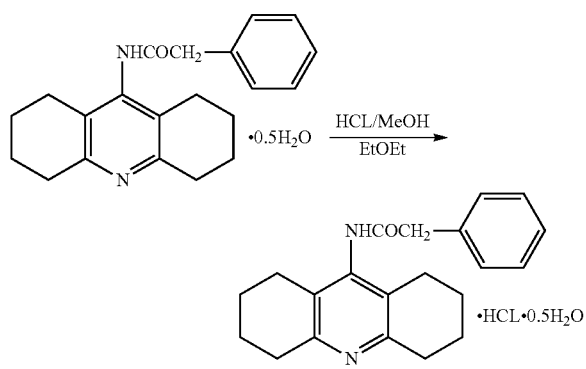

First, 1.0 g of 1,2,3,4,5,6,7,8-octohydro-9-phenylacetamidoacridine was dissolved in a minimal amount of HCL-methanol solution. A white precipitate was produced after diethyl ether was added. Following filtration, the precipitate was dried at 90° C. to generate a white crystal, i.e. the hydrochloride of 1,2,3,4,5,6,7,8-octohydro-9-phenylacetamidoacridine.

Figure 3:
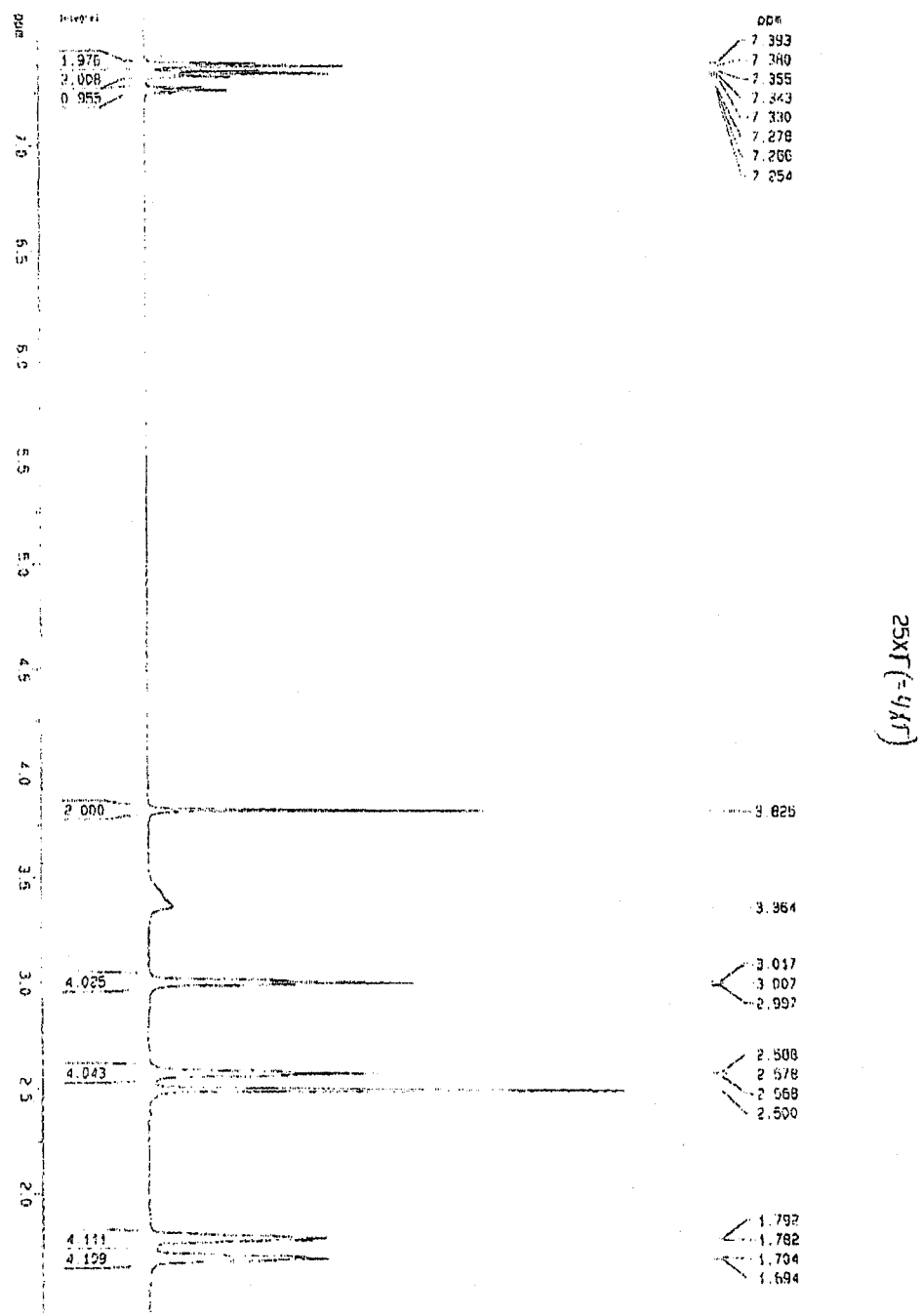
FIG. 3 is the $^1$H-NMR spectrum of the hydrochloride of 1,2,3,4,5,6,7,8-octohydro-9-phenylacetamidoacridine.
Figure 4:
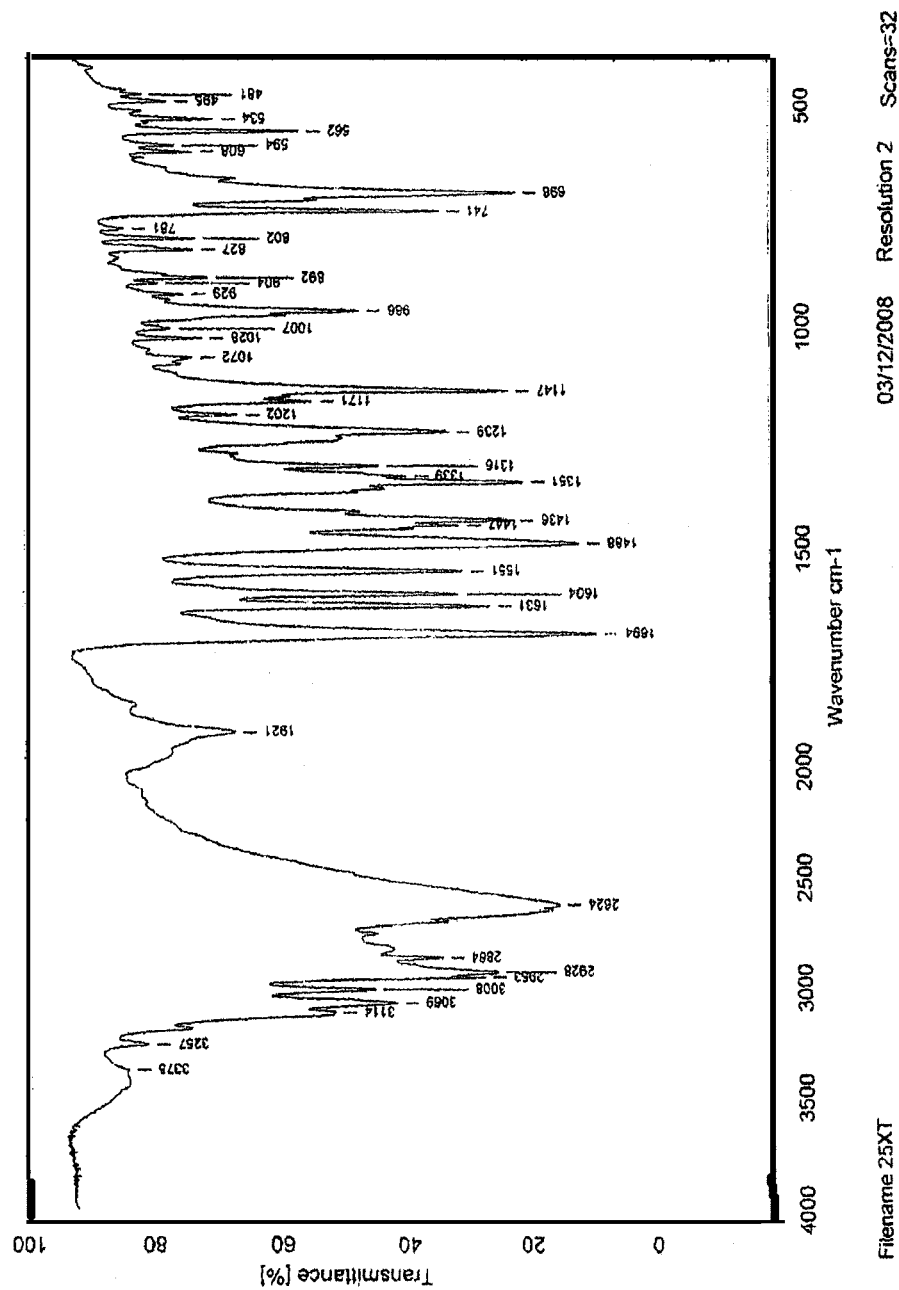
FIG. 4 is the infrared spectrum of the hydrochloride of 1,2,3,4,5,6,7,8-octohydro-9-phenylacetamidoacridine.

Molecular formula: $C_{21}H_{24}N_2O.HCL.0.5H_2O$; molecular weight: 356.90; melting point (° C.): 231-234. The $^1$H-NMR spectrum and infrared spectrum of the compound were shown in FIGS. 3 and 4, respectively. The data in the 1H-NMR spectrum included: 15.27 (1H), 10.62 (1H), 7.25-7.40 (5H), 3.38 (2H), 2.99 (4H), 2.58 (4H), 1.78 (4H), 1.70 (4H); and the data in the infrared spectrum included: 3375, 3275, 3069, 3008, 2624c., 1921, 1694c., 1631, 1604, 1551, 1488c., 1436, 1351, 1239, 1147, 741, 698.

What is claimed is:

1. 1,2,3,4,5,6,7,8-octohydro-9-phenylacetamidoacridine comprising the following structural formula, and a pharmaceutical acceptable salt thereof:

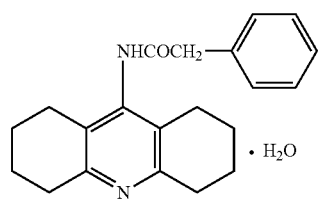

molecular formula: $C_{21}H_{24}N_2O.H_2O$; molecular weight: 338.20; melting point (° C.): 234-236.

2. The pharmaceutical acceptable salt according to claim 1, wherein the pharmaceutical acceptable salt is hydrochloride and comprises the following structural formula:

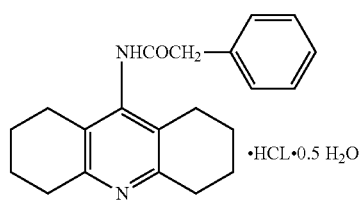

molecular formula: $C_{21}H_{24}N_2O.HCL.0.5H_2O$; molecular weight: 356.90; melting point (° C.) 231-234.

3. A method for preparing the 1,2,3,4,5,6,7,8-octohydro-9-phenylacetamidoacridine according to claim 1, comprising:
   weighting 5.0 g of 9-amino-1,2,3,4,5,6,7,8-octohydroacridine and 3.36 g of phenylacetic acid, and adding the same to a reaction bottle;
   adding 25 ml polyphosphoric acid to the reaction bottle to provide a mixture;
   heating the mixture to a temperature of 110-130° C. and allowing to react for 5 hours;
   adding about 1000 ml water after the reaction;
   adjusting pH to pH 5~6 with a KOH solution to generate a white precipitate;
   filtering off and drying the white precipitate;
   recrystallizing the white precipitate with methanol and acetone; and
   filtering off the recrystallized precipitate to generate 1,2,3,4,5,6,7,8-octohydro-9-phenylacetamidoacridine.

4. A method for preparing the hydrochloride of 1,2,3,4,5,6,7,8-octohydro-9-phenylacetamidoacridine according to claim 2, comprising:
   dissolving 1.0 g of 1,2,3,4,5,6,7,8-octohydro-9-phenylacetamidoacridine in a minimal amount of HCL-methanol solution to provide a first solution;
   adding diethyl ether to the first solution to generate a white precipitate; and filtering off and drying the white precipitate at 90° C. to generate a white crystal, comprising the hydrochloride of 1,2,3,4,5,6,7,8-octohydro-9-phenylacetamidoacridine.

5. A method of treating arrhythmia in a subject in need of such treatment comprising:
administering a composition comprising 1,2,3,4,5,6,7,8-octohydro-9-phenylacetamidoacridine according to claim 1 to the subject.

6. A method of treating arrhythmia in a subject in need of such treatment comprising:
administering a composition comprising the pharmaceutical acceptable salt according to claim 2 to the subject.

* * * * *